(12) United States Patent
Doria et al.

(10) Patent No.: US 10,564,147 B2
(45) Date of Patent: Feb. 18, 2020

(54) MICROFLUIDIC SYSTEMS FOR PARTICLE TRAPPING AND SEPARATION USING CAVITY ACOUSTIC TRANSDUCERS

(71) Applicant: The Regents of the University of California, Oakland, CA (US)

(72) Inventors: Arlene Doria, Irvine, CA (US); Maulik Patel, Irvine, CA (US); Nicholas E Martin, Irvine, CA (US); Yuka Okabe, Irvine, CA (US); Abraham Lee, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 114 days.

(21) Appl. No.: 14/403,539

(22) PCT Filed: May 24, 2013

(86) PCT No.: PCT/US2013/042735
§ 371 (c)(1),
(2) Date: Nov. 24, 2014

(87) PCT Pub. No.: WO2013/177560
PCT Pub. Date: Nov. 28, 2013

(65) Prior Publication Data
US 2015/0219623 A1    Aug. 6, 2015

Related U.S. Application Data

(60) Provisional application No. 61/652,020, filed on May 25, 2012.

(51) Int. Cl.
*G01N 33/49* (2006.01)
*B01D 43/00* (2006.01)
(Continued)

(52) U.S. Cl.
CPC ......... *G01N 33/5005* (2013.01); *B01D 43/00* (2013.01); *B01L 3/502761* (2013.01);
(Continued)

(58) Field of Classification Search
None
See application file for complete search history.

(56) References Cited

U.S. PATENT DOCUMENTS 2,656,508 A    10/1953 Coulter
3,380,584 A    4/1968 Fulwyler
(Continued)

FOREIGN PATENT DOCUMENTS

GB    2395196    5/2004
WO    WO2007120240 A2    10/2007
(Continued)

OTHER PUBLICATIONS

Lee, A. P. et al. "Microfluidic Air-Liquid Cavity Acoustic Transducers for On-Chip Integration of Sample Preparation and Sample Detection," Journal of Laboratory Automation, Dec. 2010, vol. 15, No. 6, 449-454.*
(Continued)

*Primary Examiner* — Christopher Adam Hixson
*Assistant Examiner* — Michelle Adams
(74) *Attorney, Agent, or Firm* — Nguyen Tarbet

(57) ABSTRACT

Novel systems and methods are provided that rapidly separate particles from a liquid. In an embodiment, a small volume of liquid (such as a blood sample, or any other solution with a concentration of particles) is input into a flow device implemented as a unilateral channel. When activated by an acoustic energy source (such as an ultrasound pulse), gas-liquid interfaces naturally occurring between the liquid in the flow device and a plurality of gas-filled cavities that line the channel will oscillate and create stable cavitation
(Continued)

streaming within a localized region of the surrounding liquid. These oscillations create micro-vortices that gently remove and trap particles and debris from the liquid and adjacent surfaces. Fluid and particle manipulation can thus be accomplished on a passive, disposable chip that is placed on top of an external acoustic transducer with a coupling medium.

13 Claims, 6 Drawing Sheets

(51) Int. Cl.
  *G01N 33/50*  (2006.01)
  *B01L 3/00*  (2006.01)
(52) U.S. Cl.
  CPC .... *G01N 33/491* (2013.01); *B01L 2200/0668* (2013.01); *B01L 2300/0816* (2013.01); *B01L 2300/0883* (2013.01)

(56) References Cited

U.S. PATENT DOCUMENTS

| | | | |
|---|---|---|---|
| 4,009,435 | A | 2/1977 | Hogg |
| 5,465,582 | A | 11/1995 | Bliss et al. |
| 8,263,023 | B2 | 9/2012 | Le Vot et al. |
| 8,365,311 | B2 | 1/2013 | Nawarathna |
| 8,927,040 | B2 | 1/2015 | Brand et al. |
| 9,176,504 | B2 | 11/2015 | Chiou et al. |
| 2002/0182654 | A1 | 12/2002 | Jing et al. |
| 2004/0234588 | A1 | 11/2004 | Lu et al. |
| 2005/0015001 | A1 | 1/2005 | Lec et al. |
| 2005/0106064 | A1 | 5/2005 | Laurell et al. |
| 2005/0272039 | A1 | 12/2005 | Yasuda |
| 2005/0272096 | A1 | 12/2005 | Clague et al. |
| 2006/0051329 | A1 | 3/2006 | Lee et al. |
| 2006/0177815 | A1 | 8/2006 | Soh et al. |
| 2007/0264320 | A1 | 11/2007 | Lee et al. |
| 2008/0038807 | A1 | 2/2008 | Pommersheim |
| 2008/0241875 | A1 | 10/2008 | Hwang et al. |
| 2009/0042310 | A1 | 2/2009 | Ward et al. |
| 2009/0068170 | A1 | 3/2009 | Weitz et al. |
| 2009/0075390 | A1 | 3/2009 | Linder et al. |
| 2009/0286300 | A1 | 11/2009 | Le Vot et al. |
| 2009/0298191 | A1 | 12/2009 | Whitesides et al. |
| 2010/0078384 | A1* | 4/2010 | Yang .............. B01D 21/283 |
| 2011/0059556 | A1 | 3/2011 | Strey et al. |
| 2011/0086352 | A1 | 4/2011 | Bashir et al. |
| 2011/0285042 | A1 | 11/2011 | Viovy et al. |
| 2012/0001434 | A1* | 1/2012 | Oshkai .............. F03B 13/141 290/54 |
| 2012/0034155 | A1 | 2/2012 | Hyde et al. |
| 2012/0107912 | A1 | 5/2012 | Hwang et al. |
| 2012/0196288 | A1 | 8/2012 | Beer |
| 2013/0078163 | A1 | 3/2013 | Chung et al. |
| 2013/0154671 | A1 | 6/2013 | Lee et al. |
| 2013/0171628 | A1 | 7/2013 | Di Carlo et al. |
| 2013/0210649 | A1 | 8/2013 | McKnight et al. |
| 2013/0330247 | A1* | 12/2013 | Wilson ............ B01L 3/502707 422/504 |
| 2014/0011291 | A1 | 1/2014 | Patel et al. |
| 2014/0068797 | A1 | 3/2014 | Doudna et al. |
| 2014/0076430 | A1 | 3/2014 | Miller et al. |
| 2015/0018226 | A1 | 1/2015 | Hansen et al. |
| 2016/0033378 | A1 | 2/2016 | Husain et al. |
| 2016/0123858 | A1 | 5/2016 | Kapur et al. |
| 2016/0202153 | A1 | 7/2016 | Gadini et al. |
| 2017/0014449 | A1 | 1/2017 | Bangera et al. |
| 2017/0128940 | A1 | 5/2017 | Amini et al. |
| 2017/0145169 | A1 | 5/2017 | Oakey et al. |
| 2017/0183722 | A1 | 6/2017 | Link |
| 2018/0030515 | A1 | 2/2018 | Regev et al. |
| 2018/0078940 | A1 | 3/2018 | Lee et al. |

FOREIGN PATENT DOCUMENTS

| | | |
|---|---|---|
| WO | WO2015157567 A1 | 10/2015 |
| WO | WO2016040476 A1 | 3/2016 |
| WO | WO2016126871 A2 | 8/2016 |
| WO | WO2017070169 A1 | 4/2017 |

OTHER PUBLICATIONS

Tovar, A.R. et al. "Lateral cavity acoustic transducer," Lab on a Chip, 2009, 9, 41-43. (Year: 2009).*
Okabe, Y. "Cavitation acoustic transducers (CATs) for DNA biosensors," University of California, Irvine, ProQuest Dissertations Publishing, 2012. 3542723. (Year: 2012).*
Tovar, A.R. et al. "Lateral Cavity Acoustic Transducer," Twelfth International Conference on Miniaturized Systems for Chemistry and Life Sciences, Oct. 12-16, 2008, San Diego, California, USA, 1384-1386. (Year: 2008).*
Search.ProQuest.com Abstract/Details webpage for "Cavitation acoustic transducers (CATs) for DNA biosensors" by Okabe, Yuka. University of California, Irvine, ProQuest Dissertations Publishing, 2012. 3542723. Downloaded from the internet on Jun. 22, 2019 (Year: 2019).*
International Search Report for PCT Application No. PCT/US18/56852 dated Jan. 11, 2019.
Lin, R., et al. "High efficiency cell encapsulation utilizing novel on-demand droplet generation scheme and impedance-based detection." 14th international conference on miniaturized systems for chemistry and life sciences, ed. H. Andersson-Svahn, S. Verpoorte, J. Emineus, N. Pam ma 2010.
J. Kim, M. Chung, S. Kim, D. H. Jo, J. H. Kim, and N. L. Jeon, "Engineering of a Biomimetic Pericyte-Covered 3D Microvascular Network," Plos One, vol. 10, p. e0133880, 2015.
X. Wang, D. T. T. Phan, A. Sobrino, S. C. George, C. C. W Hughes, and A. P. Lee, "Engineering anastomosis between living capillary networks and endothelial cell-lined microfluidic channels," Lab on a Chip, vol. 16, pp. 282-290, 2016.
Mazutis, L. et al., Lab on a Chip, vol. 9, pp. 2665-2672 (2009).
Simon, M.G. et al., Label-Free Detection of DNA Amplification in Dropletsusing Electrical Impedance, 15th International Conference on Miniaturized Systems for Chemistry and Life Sciences 2011 (MicroTAS 2011), pp. 1683-1685 (Year: 2011).
Marsh et al. Room temperature ionic liquids and their mixtures—a review. Fluid Phase Equilibria 219 (2004) 93-98.
Oh, Woon Su, "Synthesis and applications of imidazolium-based ionic liquids and their polymer derivatives" (2012). Doctoral Dissertations. 1958. http://scholarsmine.mst.edu/doctoral_dissertations/1958.
Baret et. al, "Fluorescence-activated droplet sorting (FADS): efficient microfluidic cell sorting based on enzymatic activity," Lab Chip. Jul. 7, 2009; 9(13):1850-8. doi: 10.1039/b902504a. Epub Apr. 23, 2009.
Macosko et al., "Highly Parallel Genome-wide Expression Profiling of Individual Cells Using Nanoliter, Droplets," Cell, vol. 161, No. 5, pp. 1202-1214, May 2015.
International Search Report for PCT Application No. PCT/US18/36962 dated Aug. 30, 2018.
International Search Report for PCT Application No. PCT/US18/36952 dated Sep. 18, 2018.
Inexpensive Droplet-Based Microfluidic Platform. CIDAR lab. https://www.youtube.com/watch?v=aHvfEOlh_b4, video description only. Mar. 14, 2017.
Kamalakshakurup et al. High-efficiency single cell encapsulation and size selective capture of cells in picoliter droplets based on hydrodynamic micro-vortices. Lab Chip, 2017, 17, 4324-4333.
Brouzes, Eric, et al. "Droplet microfluidic technology for single-cell high-throughput screening." Proceedings of the National Academy of Sciences106.34 (2009): 14195-14200.
S. I. Rubinow and J. B. Keller, "The transverse force on a spinning sphere moving in a viscous fluid," J. Fluid Mech., vol. 11, No. 03, p. 447, Nov. 1961.

(56) References Cited

OTHER PUBLICATIONS

Murata et al., Electrochemical single-cell gene-expression assay combining dielectrophoretic manipulation with secreted alkaline phosphatase reporter system, 2009, Biosensors and Bioelectronics, 25, 913-919.
Stinson et al., Genes Expressed in the Male Gametophyte of Flowering Plants and Their Isolation, 1987, Plant Physiol., 83, 442-447.
International Search Report for PCT Application No. PCT/US2016/056683 dated Dec. 27, 2016.
International Search Report for PCT Application No. PCT/US18/55722 dated Feb. 6, 2019.
International Search Report for PCT Application No. PCT/US17/55984 dated Dec. 14, 2017.
Doria, Arlene et al., "Rapid blood plasma separation with air-liquid cavity acoustic transducers", 15th International conference on miniaturized systems for chemistry and life sciences, Oct. 2-6, 2011, pp. 1882-1884.
Lee, Abraham P. et al., "Microfluidic air-liquid cavity acoustic transducers for on-chip integration of sample preparation and sample detection", Journal of laboratory automation, Dec. 2010, vol. 15, No. 6, pp. 449-454.
International Search Report Issued for PCT Application No. PCT/US2013/042735 dated Nov. 28, 2013.

\* cited by examiner ic SYSTEMS FOR PARTICLE TRAPPING AND SEPARATION USING CAVITY ACOUSTIC TRANSDUCERS

CLAIM OF PRIORITY

This application claims priority to PCT Application PCT/US2013/042735 entitled, "MICROFLUIDIC SYSTEMS FOR PARTICLE TRAPPING AND SEPARATION," filed May 24, 2013, which claims the benefit of U.S. provisional application entitled, "MICROFLUIDIC SYSTEM FOR PARTICLE TRAPPING AND SEPARATION FOR NON-BIOLOGICAL AND BIOLOGICAL PROCESSES," filed May 25, 2012, application No. 61/652,020, all of which are incorporated by reference in its entirety and for all purposes.

BACKGROUND

Medical testing has long been a staple in healthcare, and often serves as the starting point for providing diagnostic and (if necessary) ameliorative or palliative care. For certain conditions, testing using fluid samples collected from a patient have become the preferred method for analysis. Rapid diagnostic tests (RDTs) at point-of-care (POC) are one type of medical testing. Though convenient, the usage of RDTs has several main critiques that prevent such applications from being more widely adopted relative to centralized laboratory testing. These critiques range from a perceived higher cost and lower accuracy and precision of RDTs relative to central laboratory tests; issues with data traceability due to lack of device connectivity; and a potentially higher incidence rate of operator error. While recent POC devices have attempted to address some of these issues with lower material costs, data transmission capabilities, and improved standards and qualifications, concerns regarding performance and reliability still persist.

The POC market is comprised of many lateral flow or passive flow-through devices. These are technologies that use capillary-driven flow to perform assays on fluid samples. Passive flow generally limits these devices from yielding precise, quantitative results. Likewise, lateral flow devices provide only qualitative or semi-quantitative results due to a limited control of reagent and sample handling that could otherwise be used to optimize assay conditions. The use of additional components such as external pumps to accomplish active flow control capabilities or new biosensors to increase sensitivity can be used to mitigate these disadvantages, but would also add complexity into the manufacturing process that may be undesirable.

The ability to perform sample preparation on fluids such as separating and/or extracting particles and cells based on size is highly desirable for a rapid diagnostic. Separation processes for diagnostics may include centrifugation, filtration, precipitation, adsorption, chromatography, and extraction for separating by particles by size, density, shape, viscosity, and other physical and chemical properties. Centrifugation has long been the standard lab technique for separating particles. However, centrifugation equipment is not suitable for POC applications. Moreover, operators can often encounter difficulties when centrifuging small sample volumes because samples are easily lost during pipetting and decanting steps. Automated robotic sampling can address the issues with handling small sample volumes however; these machines are costly and can be inefficient or even prohibitive for many healthcare providers. The other methods of separation require special chemistries and handling which would introduce operator errors and quantitative inaccuracies and imprecision in the results of the diagnostic device.

Blood sample preparation is another important step when developing a point-of-care diagnostic device. Rapid plasma extraction from whole blood is required to prevent cellular components from interfering with the detection analysis which is often performed optically in a POC device. In rapid diagnostic devices, commercially available filters are integrated into the device to extract plasma. However, manufacturing these filters requires complex and costly processing with multiple reagents. Other microfluidic strategies to extract plasma include the bifurcation law, hydrodynamics, filtration, and magnetophoresis. Unfortunately, many of these strategies have practical limitations in cost, time, scale-up, and plasma yield that make them less than ideal.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Various embodiments of the claimed subject matter are directed to manipulating particles in a volume of fluid. According to a first aspect of the claimed subject matter, a novel device is provided that rapidly separates particles from a liquid. In an embodiment, a small volume of liquid (such as a blood sample, or any other solution with a concentration of particles) is input into a flow device implemented as a unilateral channel. When activated by an acoustic energy source (such as an ultrasound pulse), gas-liquid interfaces naturally occurring between the liquid in the flow device and a plurality of gas-filled cavities that line the channel will oscillate and create stable acoustic microstreaming within a localized region of the surrounding liquid. These oscillations create micro-vortices that gently remove and trap particles and debris from the liquid and adjacent surfaces. Fluid and particle manipulation can thus be accomplished on a passive, disposable chip that is placed on top of an external acoustic transducer with a coupling medium.

The oscillating gas-liquid interfaces are named cavity acoustic transducers (CATs). CATs can be engineered in a microfluidic design by designing the device to include dead-end cavities of any shape, volume, and spacing and at any angle incident to the main channel. This level of control allows directed streaming capabilities and may be designed specifically for various applications. For example, when blood is pumped through an array of rectangular CATs angled at 15 degrees incident to the main channel, plasma separation can be achieved. According to this embodiment, the red blood cells are trapped within the vortices as plasma continues to flow downstream, effecting a separation of cells from the plasma that is visible at the leading end of the flow.

According to another aspect of the claimed subject matter, a microfluidic device is provided that uses gas-liquid cavity acoustic transducers (CATs) for a particle based assay such as agglutination. In one embodiment, the device may be used to quantify concentrations of any analyte such as C-reactive protein (CRP), a general marker of inflammation or infection. This novel detection method relies on CATs to produce microvortices that trap particles coated with a capture reagent (such as antibodies or aptamers that are labeled or label-free) and induce binding of the analyte. Using CAT microstreaming, the particle based assay is enhanced through mixing while the particles are contained and measured in microvortices.

In a still further aspect of the claimed subject matter, a plurality of CATs in a flow device is used for cell separation and micropumping of a reagent to achieve sample preparation or detection. According to yet another aspect of the invention, a device is provided using gas-liquid cavity acoustic transducers (CATs) with a tunable parameter that is operable to lyse cells and then extract the sample without the remaining cellular debris. By varying the input voltages applied to the acoustic transducer, CATs can be tuned to first lyse particles such as cells and then to separate the components from the solution.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, combinations, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, materials, and circuits have not been described in detail as not to unnecessarily obscure aspects and features of the subject matter.

Portions of the detailed description that follow are also presented and discussed in terms of a process. Although steps and sequencing thereof are disclosed in figures herein (e.g., FIG. 6) describing the operations of this process, such steps and sequencing are exemplary. Embodiments are well suited to performing various other steps or variations of the steps recited in the flowchart of the figure herein, and in a sequence other than that depicted and described herein.

Fluid-Based Particle Manipulation

Figure 1:
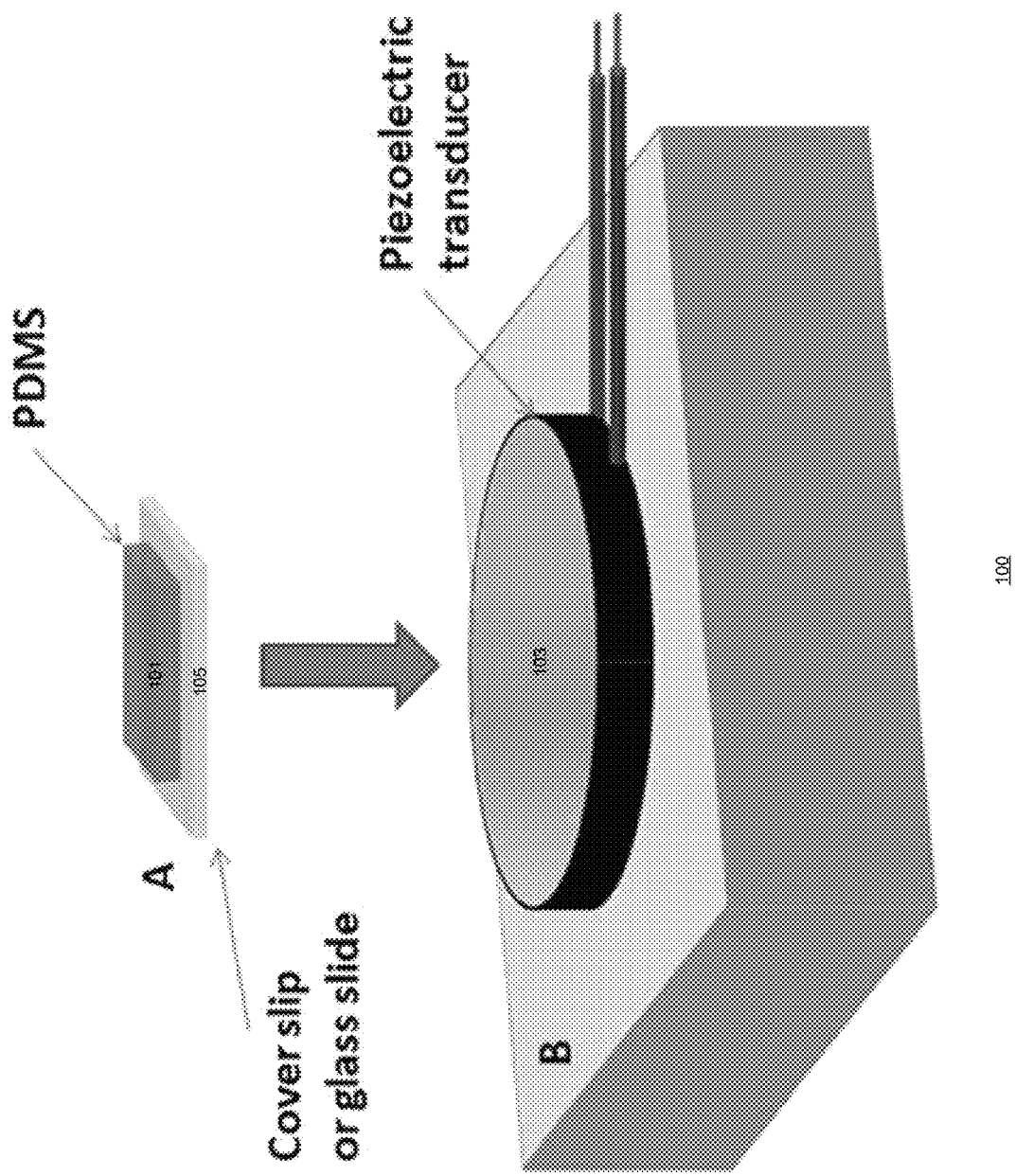
FIG. 1 is an illustration of an exemplary system for fluid-based particle manipulation, in accordance with various embodiments of the claimed subject matter.

FIG. 1 is an illustration of an exemplary microfluidic system 100 for fluid-based particle manipulation. As depicted in FIG. 1, a small volume of liquid (such as a blood sample, or any other solution with a concentration of particles) is input into a microfluidic passive flow device 101. According to some embodiments, the microfluidic device 101 may be made of polydimethylsiloxane (PDMS) and fabricated using standard soft lithography techniques. In alternate embodiments, the microfluidic device 101 may be fabricated from any number of suitable materials and compositions including, but not limited to polymers, metals, ceramics, or combinations there of. In still further embodiments the device 101 may be bonded to a glass cover slip 105, using plasma, for example. According to one embodiment, the device 101 is disposed on, and coupled to an acoustic energy source, such as a piezoelectric transducer 103 using ultrasound gel.

Particle separation for particles in a liquid inserted (e.g. via wicking, or pipetting) into the device 101 is accomplished by producing ultrasound from an acoustic energy source and activating gas-liquid cavity acoustic transducers (CATs) that form naturally in hydrophobic devices filled with liquids. This causes gas-liquid interfaces within the microfluid device 101 to oscillate and create stable cavitation streaming within a localized region of the surrounding liquid. These oscillations create micro-vortices that gently remove and trap particles and debris from the liquid and adjacent surfaces. According to further embodiments, surfactants may be used to stabilize the gas-liquid interfaces of the CATs. Surfactants assemble on a surface of a bubble to lower the surface tension that normally would cause the bubble to collapse. Surfactants can include polysorbates, sodium dodecyl sulfate, lauryl dimethyl amine oxide, mono and diesters of sucrose stearate, and others. In alternate embodiments, gases like perfluorocarbons or nitrogen, which have low solubility may also be used to stabilize the bubble. In still further embodiments, nanoparticles or lipid structures that assemble around the bubble can also be used to extend the bubble's stability.

Because CAT microstructures can be fabricated in only a single layer, they are amenable to conventional manufacturing processes—such as such as hot embossing, injection molding, lamination, and casting—that require relatively inexpensive parts. Furthermore, piezoelectric transducers as fluidic drivers are durable because no moving parts are required. Finally, the simplicity of such a design will allow this separation technology to be integrated into various lab-on-chip assays.

Figure 2:
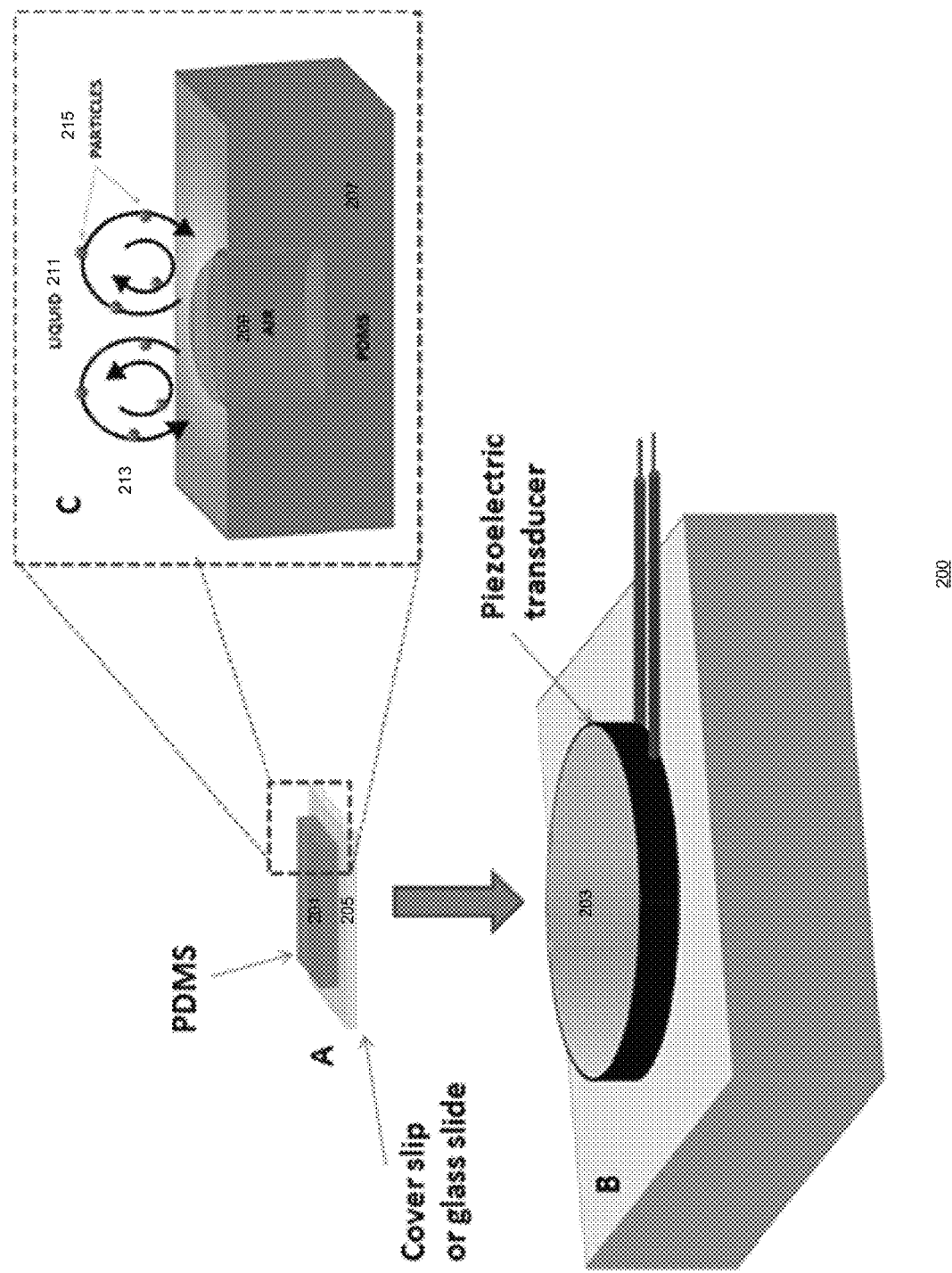
FIG. 2 is an illustration of an exemplary system for fluid-based particle manipulation that depicts an gas-liquid interface, in accordance with various embodiments of the claimed subject matter.

FIG. 2 depicts an alternate illustration of the system described above with respect to FIG. 1. FIG. 2 likewise depicts a microfluidic passive flow device 201 bonded to a glass cover slip 205 which in turn is disposed over and coupled (via an ultrasound gel or other medium, for example) to an acoustic energy source 203. FIG. 2 also depicts a magnified illustration of a cross section of a portion 207 of the device 201. As depicted in the cross section, cavities 209 are formed in the portion of the device 207, and naturally fill with gas. These cavities 209 may be manufactured with any shape, volume, and spacing at a pre-determined angle incident to the flow of a liquid 211 through a channel in the device 201. Ultrasound energy produced by acoustic energy source 203 oscillates the gas-liquid interface between the gas in the cavities 209 and the liquid 211 flowing through the channel, in turn causing the generation of a plurality of micro-vortices 213. Particles 215 in the liquid become trapped in the micro-vortices as the liquid flows past.

Figure 3:
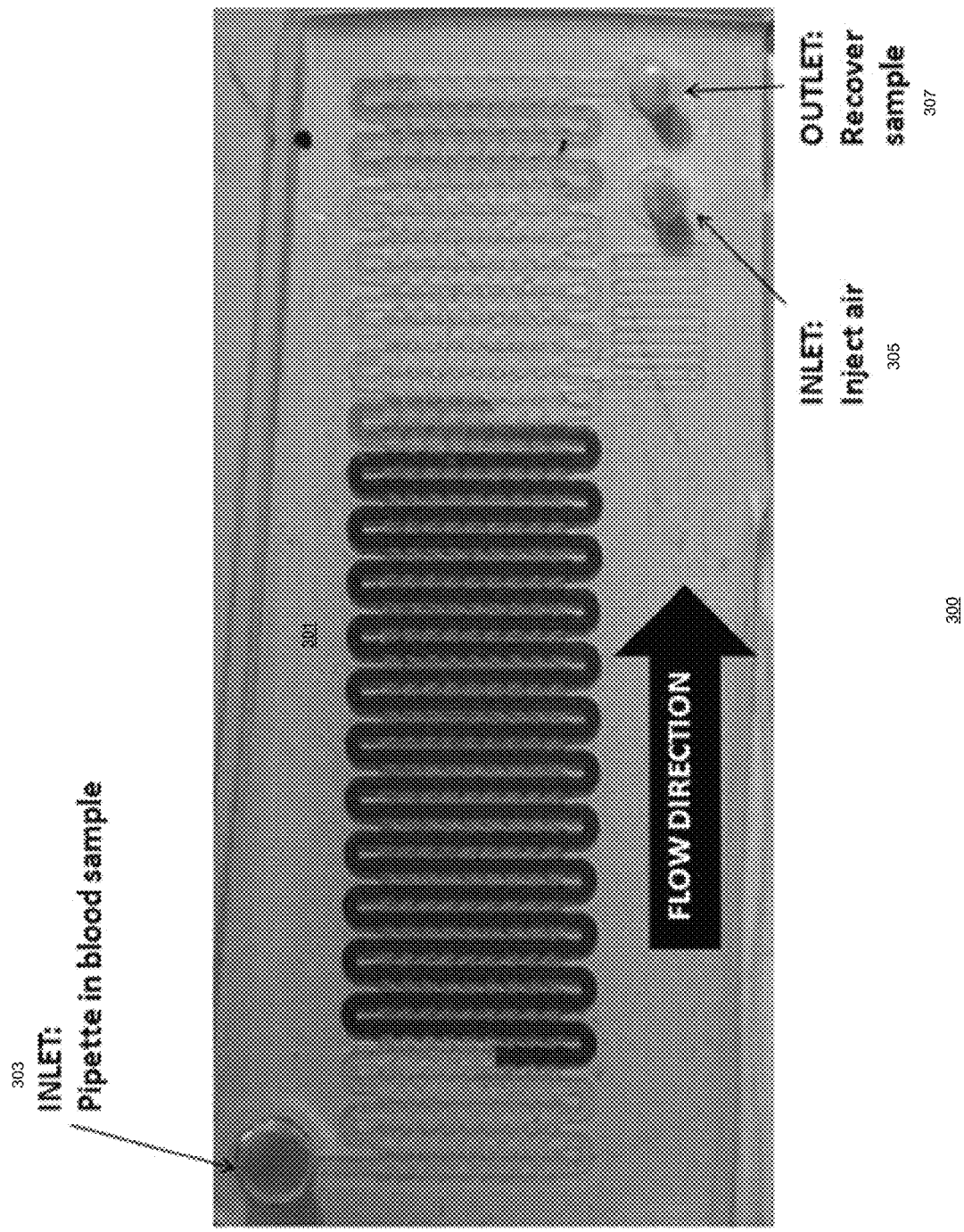
FIG. 3 is an illustration of an exemplary device comprising a channel and a plurality of micro-cavities, in accordance with various embodiments of the claimed subject matter.

FIG. 3 is an illustration of an exemplary device 300 comprising a channel 301 and a plurality of micro-cavities, in accordance with various embodiments of the claimed subject matter. Exemplary device 300 may comprise one implementation of the microfluidic device described above with respect to FIGS. 1 and 2. As depicted in FIG. 3, the device 300 may include one or more inlets (e.g., inlet 303, 305) that allow the insertion of liquids (via inlet 303) or gas (via inlet 305). According to some embodiments, the device may also include an outlet 307, which may be used to recover the sample liquids introduced via inlet or used for waste 303.

In an embodiment, the channel 301 is arranged as a serpentine channel, with an array of CATs lining the channel on one or more sides. In a further embodiment, these CATs may be arranged parallel to each other. According to other embodiments, the channel 301 may be arranged in alternate configurations, and may comprise additional channels and/or alternate orientations of CATs. As depicted in FIG. 3, the CATs may be angled toward the direction of flow. According to other embodiments, the orientation of the CATs may be angled away from the direction of flow, or perpendicular to the direction of flow. When the device 301 is filled with liquid, CATs trap bubbles creating an gas-liquid interface that can be excited by an external acoustic energy source (such as a piezoelectric transducer). The oscillations of the gas-liquid interface will generate a first-order periodic flow which will induce a steady second-order microstreaming flow. Based on the particular shape, angle, volume, and spacing of the CATs, the acoustic microstreaming generates a bulk flow in the microchannel.

Due to the acoustic microstreaming, oscillation of the gas-liquid interface results in a first order periodic flow. At the gas-liquid boundary, the velocity is at its maximum. This velocity is approximately proportional to the amplitude of the oscillation times the angular frequency of the gas-liquid interface that is actuated by the acoustic source. The consequence of a steady first-order periodic flow is that it induces steady second order flow which includes microvortices. It is within these second order flow fields where particles such as cells are manipulated or trapped. As particles get trapped and concentrated in these vortices while flow is in the channel, various methods may be applied to these particles (particle separation, lysing, filtering, etc).

The vortices generated are also capable of trapping particles and cells. This is due to the fact that shear gradient lift forces within the vortices cause particles to flow towards the center of the vortex. This shear gradient lift force is dependent on the size and density of the particles, with larger particles experiencing a larger force. Voltages applied to the piezoelectric transducer determine both the bulk flow velocity and the acoustic microstreaming velocity simultaneously which result in different particle trapping efficiencies.

Figure 4:
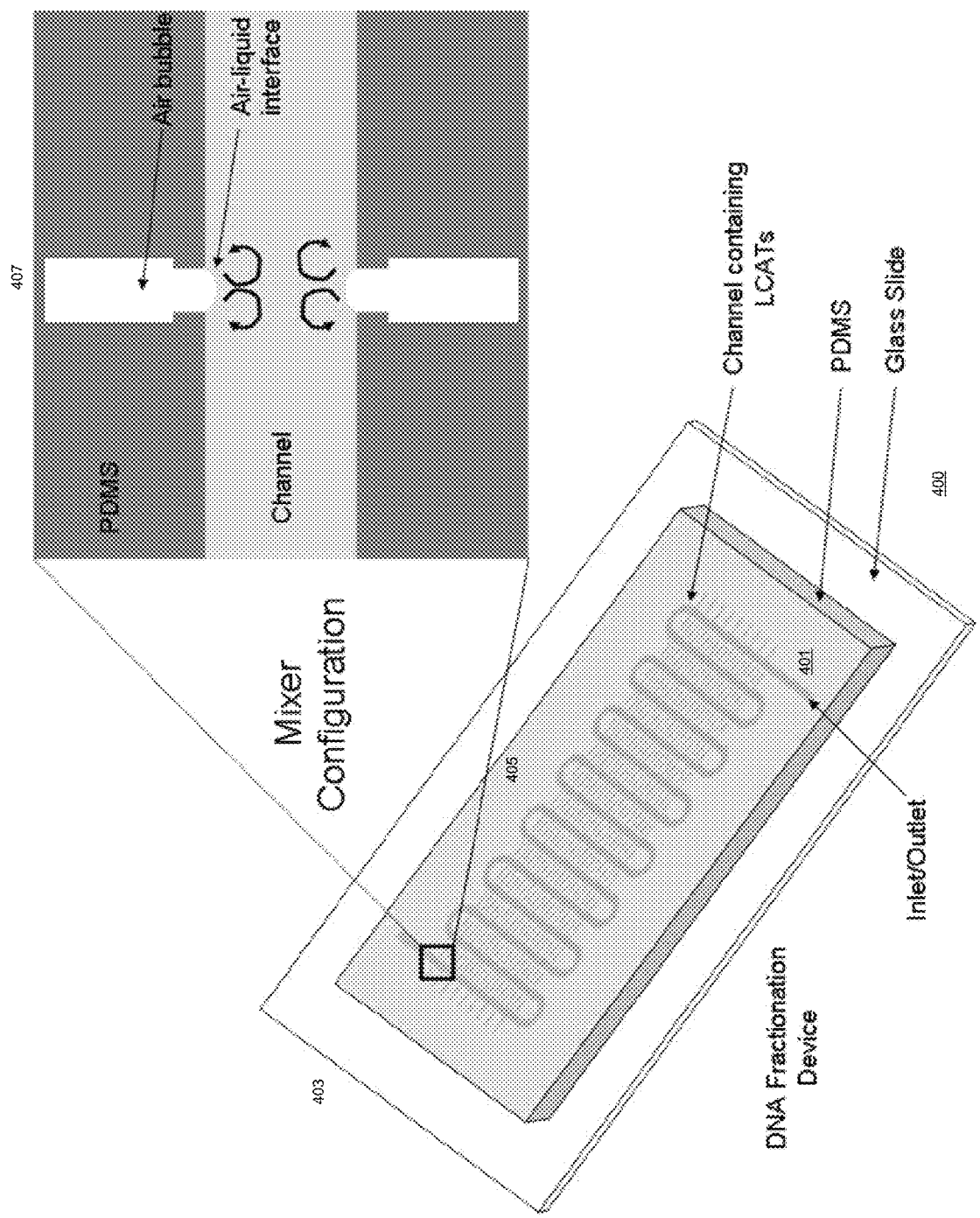
FIG. 4 is an illustration of an exemplary configuration of CATs in a system for fluid-based particle manipulation, in accordance with various embodiments of the claimed subject matter.

FIG. 4 depicts an illustration of an exemplary configuration of CATs in a system 400 for fluid-based particle manipulation, in accordance with various embodiments of the claimed subject matter. As depicted in FIG. 4, the system 400 includes a microfluidic device 401, disposed over (and in some embodiments, bonded to) a glass slide 403. The device 401 itself may consist of a fluid channel 405. FIG. 4 also depicts a magnified portion of the device 401, which depicts an alignment of a pair of CATs 407 that is perpendicular to the channel 405.

Figure 5:
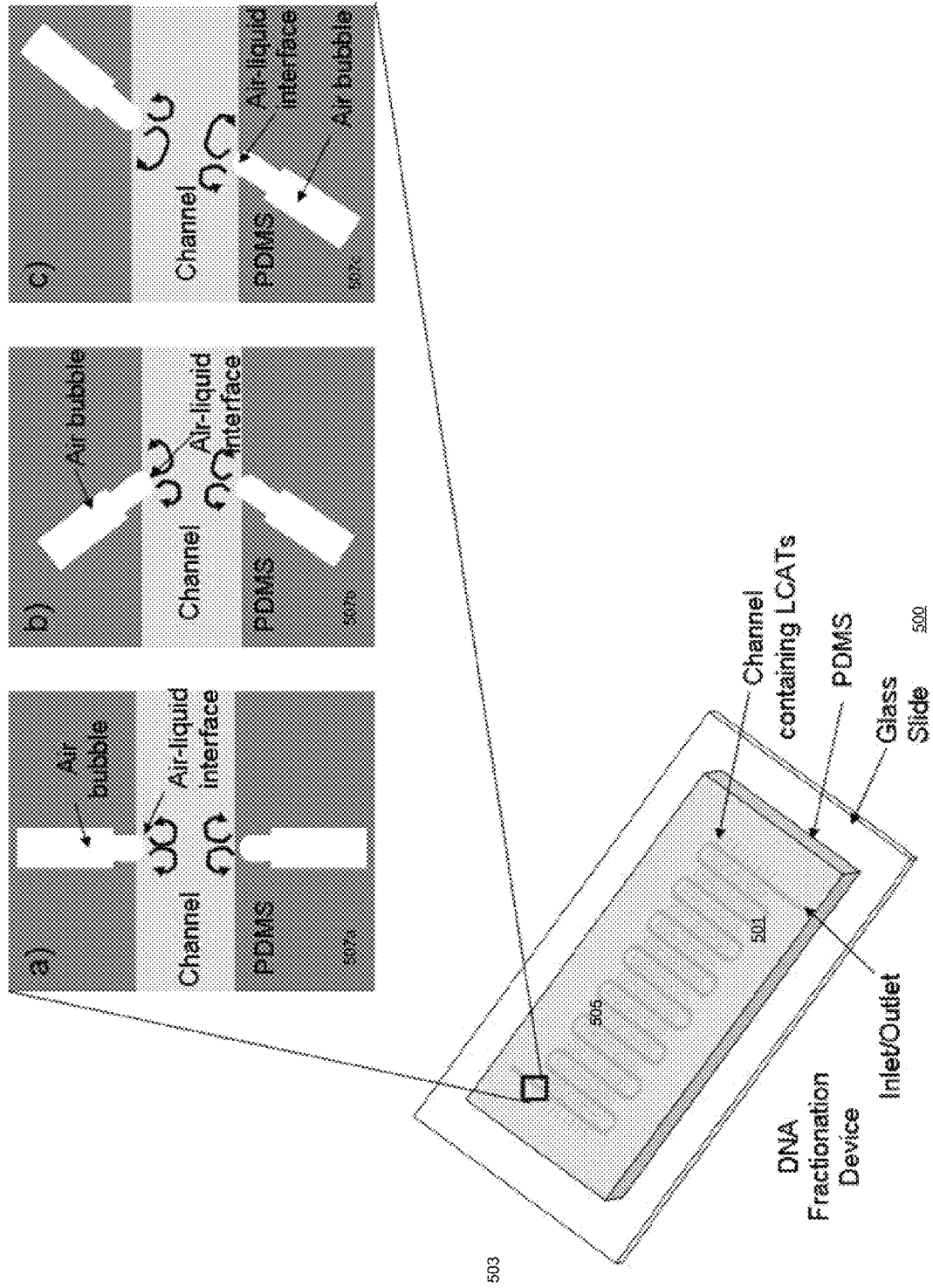
FIG. 5 is an illustration of multiple configurations of CATs in a system for fluid-based particle manipulation, in accordance with various embodiments of the claimed subject matter.

FIG. 5 is an illustration of multiple configurations of micro-cavities in a system 500 for fluid-based particle manipulation, in accordance with various embodiments of the claimed subject matter. As depicted in FIG. 5, the system 500 includes a microfluid device 501 disposed over (and in some embodiments, bonded to) a glass slide 503. The device 501 itself may consist of a fluid channel 505. FIG. 5 also depicts alternate magnified portions of the device 501, which depict various alignments (a, b, and c) of a pair of CATs (e.g., 507a, 507b, and 507c) that are perpendicular, directed with the flow of the liquid, and directed in an asymmetric orientation with respect to the channel 405. According to some embodiments, the particular orientation relative to the channel may be designed specifically to perform one or more intended functions. These functions may include, but are not limited to, particle separation, lysing, enhancing agglutination or other particle based assay, and filtration. Each of these functions is described with greater depth below.

Acoustic Micro-Centrifuge Arrays for Rapid Particle Separation

Figure 6:
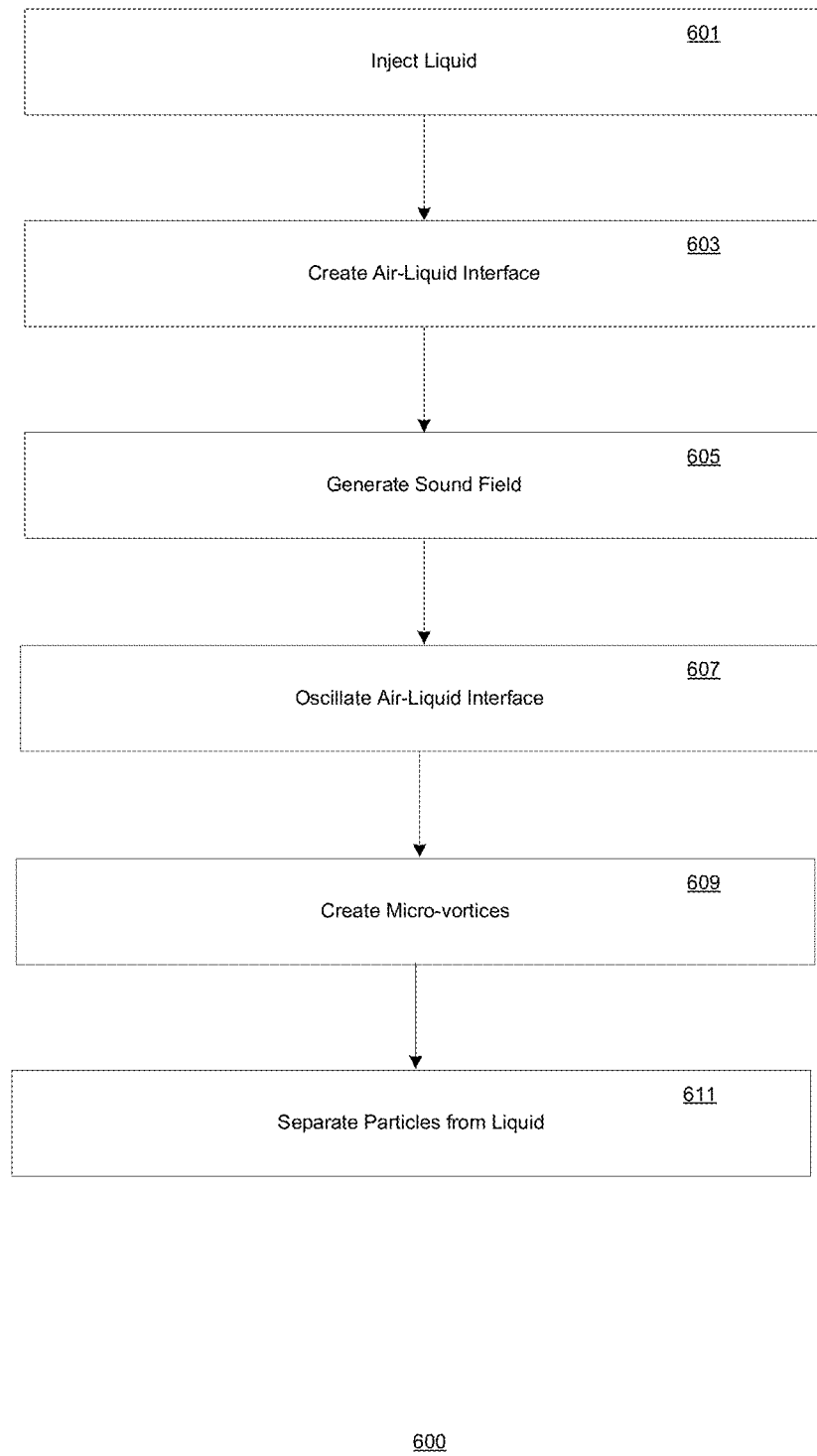
FIG. 6 is a flowchart depicting a process for manipulating particles in a fluid, in accordance with various embodiments of the claimed subject matter.

According to an embodiment, one application of the microfluid devices described herein with respect to FIGS. 1-5 is as a device capable of rapidly separating a dilute amount of particles from a liquid (e.g., blood) sample. FIG. 6 is a flowchart 600 depicting such process for manipulating particles in a fluid, in accordance with various embodiments of the claimed subject matter. Steps 601 to 611 describe exemplary steps comprising the process 600 depicted in FIG. 6 in accordance with the various embodiments herein described.

At step 601, a liquid is received in a microfluid device. In some embodiments, the liquid may be injected (via pipetting, for example) into an inlet or input terminal of the microfluid device. In further embodiments, the microfluid device may be implemented as a fluid channel with an array of micro-channels (CATs) lining the fluid channel at regular intervals and oriented at a pre-determined angle incident to the channel. As the liquid injected in step 601 continues to flow through the microfluid device, an interface (an gas-liquid interface) between the liquid and gas trapped in the CATs is created at step 603.

A sound field, produced by an acoustic source such as a piezoelectric transducer for example, is generated at step 605. In some embodiments, the microfluid device may be disposed over (or otherwise proximate) to the acoustic source. In further embodiments, the microfluid device is bonded to a surface such as a glass slide, which is coupled to the acoustic source across some medium (such as a gel). The generation of the sound field at step 605 serves to oscillate the gas-liquid interface at step 607, which in turn creates several micro-vortices (step 609) in the liquid at sites proximate to the gas-liquid interfaces. Finally, at step 611, particles in the liquid supplied during step 601 are separated. This separation is performed via the cumulative effect of thousands of microvortices generated (at step 609) by oscillating the gas-liquid cavities in the microfluid devices (at step 607). The particles become separated based on size because larger particles experience greater shear gradient lift forces from acoustic microstreaming which in turn traps them in microvortices.

Size-Based Particle Separation

According to an embodiment, another application of the microfluid devices described herein is as a novel platform that is capable of simultaneously performing on-chip pumping and trapping/separation of particles based on size. The trapping efficiency can be controlled by varying the voltage, frequency, burst mode, waveform (e.g. square, sine, triangle, or sawtooth) applied to the external transducer.

According to such embodiments, larger particles are trapped with higher efficiency within the microstreaming vortices compared to smaller particles. Smaller particles tend to occupy larger orbits within the vortices making them more likely to be influenced by viscous forces due to the bulk flow. This allows them to be released more readily to the outlet compared to larger particles. However, increasing the voltage applied to the piezoelectric transducer simultaneously increases the bulk flow velocity and the microstreaming velocity allowing larger particles to be released to the outlet as well, although to a lesser extent.

Rapid Two-Step Blood Sample Preparation

The microfluid devices described herein may be adapted to rapidly perform two-step blood sample preparation using gas-liquid cavity acoustic transducers (CATs). For example, analysis of proteins in blood such as detecting antibodies in serology tests necessitates that the blood samples be stripped of their cellular components and diluted. The standard method of sample preparation requires a centrifuge and careful pipetting techniques to transfer the sample to the analysis tool.

As described above, CATs are gas cavities that form naturally in hydrophobic devices filled with liquids. When activated by ultrasound, the gas-liquid interfaces will oscillate and create stable cavitation streaming within a localized region of the surrounding liquid. Fluid and particle manipulation can be accomplished on a passive, disposable chip that is placed on top of an external acoustic transducer with a coupling medium. In an embodiment, the CATs are used for both cell separation and micropumping of reagent such as a diluent to achieve a quick sample preparation. For example, plasma dilution is often required for analyzing immunoassays (e.g. ELISAs of antigen-spotted microarrays) because antibodies in whole blood are present in large amounts.

According to such embodiments, the sample preparation may be performed in two stages: blood plasma extraction followed by dilution with a dye. Two serpentine channels with high density CAT arrays are positioned in parallel and joined into one channel downstream.

During sample preparation, the first channel is acoustically activated to filtrate red blood cells and deliver extracted plasma to the joined channel. The second channel containing a reagent such as a diluent is then activated. Subsequently, the diluent is pumped into joined channel containing the plasma to effectively dilute the extracted plasma. With the combination of the plasma and diluent, the final diluted sample is visually distinguishable. In one embodiment, the oscillating gas-liquid interfaces create local vortices that trap red blood cells while simultaneously pumping plasma downstream effecting a net separation of cells from plasma. In the presence of the oscillating velocities, particles are trapped near the inner corners of the CAT structures.

Acoustic Manipulations of Blood Samples: Microfluidic Integration of Erythrocyte Filtration and the Detection of Rheumatoid Factor According to various embodiments, the microfluid devices described herein may also be adapted to rapidly perform a two-step agglutination assay of rheumatoid factor (RF) using CATs. As described above, CATs are trapped microbubbles that generate cavitation microstreaming when activated with ultrasound. Fluid and particle manipulation for biomolecular assays can be accomplished on a passive, disposable chip that is placed on top of an external acoustic transducer. In an embodiment, CATs may be used to rapidly filtrate red blood cells from blood followed by detection of Rheumatoid Factor using a bead assay. Rheumatoid Factor is present in a majority of patients suffering from Rheumatoid Arthritis, a chronic disease characterized by destructive joint inflammation and pain.

According to such implementations, devices are designed with two serpentine channels lined with high density CAT arrays that are angled toward the direction of the flow. The two channels are positioned in parallel and joined into one channel downstream. In some instances, the devices may be formed from polydimethylsiloxane (PDMS) and bonded to glass, and fabricated using standard soft lithography techniques. In still further embodiments, the devices may be activated using a voltage at or near 20 Vpp square waves at a frequency of 44 kHz Patterned Microcleansing and Particle Recovery with Open Acoustic Microfluidics The application of ultrasonic energy to a bath of solution is a well-established technique for improving the efficacy of cleansers and solvents. The microfluid devices described herein may be adapted to present a technique to further improve upon this method. As described above, hydrophobic PDMS devices may be made with 2D arrays of cavities that naturally trap a gas bubble when covered with aqueous solution. A piezoelectric transducer may then be used to transmit ultrasonic energy to the 2D array that oscillates the gas-liquid interface above each cavity. These oscillations create micro-vortices that gently remove and trap particles and debris from adjacent surfaces, including proteins from soiled contact lenses.

The use of these arrays to loosen and trap particles from soiled surfaces may be a useful application for microvolume cleansing of delicate components. Ultrasonic baths may be used for industrial cleaning and chemical processing. Baths requires agitation or microbubble generation that can be actuated with ultrasound. The precise location of microbubbles is not well controlled and baths require liquid volumes that exceed microliter scales. The large volume of solution required for ultrasonic baths makes the recovery of removed particles difficult. Furthermore, many sonication methods that require agitation may not be suitable for delicate surfaces. An embodiment thus consists of a device which comprises acoustically actuated bubble arrays, also referred to herein as CATs for microcleansing and particle recovery using microliter volumes.

For such a device, a high density bubble array may be fabricated using standard soft lithography techniques. Fluid and particle manipulation can be accomplished on a passive, disposable chip that is placed on top of an external acoustic transducer (in this case an electrically driven piezoelectric transducer) with a coupling medium. According to such embodiments, there is no need for a pump or external tubing.

Instead, CATs are formed by pipetting microliter volumes onto cavity arrays that trap gas bubbles. In an embodiment, a fragile, soiled contact lens may be placed on the chip with nearly conformal contact to the array. Under these circumstances, the gas-liquid interface may be modeled as an oscillating inlet/outlet. This novel method of microcleansing may serve as a niche for removing particles off delicate, soiled surfaces and recovering those particles if necessary in small microliter volumes without the need to agitate the surface to be cleaned.

Additionally, CAT arrays made with soft elastomers such as polydimethylsiloxane can be made to have conformal contact to a variety of geometric shapes. CAT microstructures can be fabricated in only a single layer and are therefore very amenable to conventional manufacturing processes.

Rapid Quantitation of Particle Based Assays Such as Agglutination Assays

A novel detection method relies on CATs to produce microvortices that trap particles that are coated with a capture reagent (such as antibodies or aptamers that are labeled or label-free) and induce binding of the analyte. Using CAT microstreaming, the particle based assay is enhanced through mixing while the particles are contained and measured in microvortices. In one embodiment, CATs are utilized to enhance agglutination assays. Conventionally, agglutination assays are qualitative because the amount of clumping is not quantified. However, light scattering (nephelometiy) and light transmission (turbidimetry) techniques have been applied to quantify the clumps. The use of microscale geometry or force fields has also been exploited in agglutination assays.

The microfluid devices described herein may also be adapted to a microfluidic device that uses gas-liquid cavity acoustic transducers (CATs) to quantify concentrations of analytes detected with a particle based assay. Using CATs microstreaming, agglutination methods may be enhanced through mixing while clumping of particles is contained and measured in microvortices. According to various embodiments, a device is provided that allows for easy quantitation of clumping at varying analyte concentrations. In one embodiment, the analytes may comprise C-reactive protein (CRP). CRP is a general marker of inflammation or infection. However, the microfluid devices described herein are well suited to be adapted for use with other analytes. For example, the microfluid devices may be used for the detection of autoimmune diseases, infection diseases, bacterial strain identification, sexually-transmitted diseases, blood typing, etc. This unique detection method relies on CATs to produce microvortices where particles get trapped.

The dynamic vortices produced by CATs can serve as detection sites for concentrated bead mixing and clumping. Specifically, CAT vortices can be used as "counters" for metering the amounts of agglutinated beads or labeled beads with captured analytes in solution. According to some embodiments, the sizes of these counters are tunable. According to these embodiments, the concentration of analyte particles in a volume of liquid can be determined by, for example, measuring the size of the particles trapped in the microvortices. Alternately, various detection methods that extend to other assays—such as optical detection (e.g., fluorescence detection) methods—may be used to determine the quantification of particles in the liquid.

Tunable Cell Lysing of Dense Blood Cell Samples with Cats

The extraction of nucleic acids and cell proteins typically requires the destruction of the cell membrane. Because the cells are suspended in solution, the solution has to be further processed to recover the components of interest after lysing. Cell lysis is the first step in nucleic acid and protein purification methods. Conventional ways to lyse cells include physical or chemical means. Cell lysis methods include mild osmosis, sanitation, centrifugation with beads, detergents, and nitrogen burst methods. However, these methods require a step to separate the remaining cellular debris. Additional handling steps increase the chances of operator error. Furthermore, the efficiency of lysing is dependent on the density of cells in the solution, the total volume of the solution, and the toughness of the cell.

The microfluid devices described herein may be adapted to lyse particles. A device using gas-liquid cavity acoustic transducers (CATs) with tunable parameters that will lyse cells and then extract the sample without the remaining cellular debris. By varying the flow through the channel and the input parameters applied to the acoustic transducer, CATs can be tuned to first lyse cells and then to separate the components from the solution.

In an embodiment, arrays of CATs line a serpentine channel. The CATs are angled toward the direction of flow. A sample undergoes lysis by applying a high input voltage (e.g., 30 Vpp) to a piezoelectric transducer while inhibiting flow by plugging the outlets. Recovery of the sample is then performed by unplugging the outlets and allowing separation of cellular debris to occur at a lower voltage.

The oscillating gas-liquid interfaces create local vortices that trap red blood cells while simultaneously pumping plasma downstream, effecting a net separation of cell debris from plasma. In the presence of the oscillating velocities, particles are trapped near the inner corners of the CAT structures. Increasing the velocities or increasing the time in transit increases the lysis index.

This novel method of cell lysing and fluid flow control is tunable and durable since no moving parts are required for the actuation of the chip. Although red blood cells are used in this application for the purposes of modeling, other cell types such as bacteria, white blood cells, tumor cells, which contain nucleic acid would be likely candidates for this application. Because this technology is performed quickly and wholly on chip, it can be integrated as a sample preparation component that can be linked to downstream analyses in point-of-care diagnostics or other lab-on-chip applications.

By using any of the systems or methods provided above, fluid and particle manipulation may be performed using inexpensive microfluidic devices with point-of-care portability and versatility that achieve an efficiency and efficacy at least on par with traditional, expensive, laboratory testing. As described above, embodiments of the claimed subject matter provide novel methods and systems to perform a plurality of functions, including particle separation, lysing, agglutination, and filtration. The devices described herein may be designed to perform one, some, or all of the plurality of functions upon a single sample.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for manipulating particles in fluids, the system comprising:
    an acoustic energy source configured to produce ultrasound;
    a device disposed over the acoustic energy source and comprising:
        a first channel;
        a first inlet into the first channel, wherein a volume of liquid that is received via the first inlet flows through the first channel; and
        a first plurality of gas-liquid cavity acoustic transducers (CATs) on a first side of the first channel and a second plurality of CATs on a second side of the first channel, wherein the first side is opposite the second side, and wherein an opening of each CAT of the first plurality of CATs is directly opposite and aligned with an opening of a respective CAT of the second plurality of CATs, wherein each CAT of the first and second pluralities of CATs is connected to the first channel at a right angle relative to the first channel, wherein for each CAT of the first and second pluralities of CATs, a gas-liquid interface is created between the volume of liquid flowing through the first channel and a respective first volume of gas in the CAT, wherein the ultrasound produced from the acoustic energy source causes the gas-liquid interface to oscillate, thereby generating a plurality of micro-vortices in the first channel;

wherein a plurality of particles in the volume of liquid are separated from the volume of liquid as the volume of liquid flows through the first channel, and wherein the plurality of particles separated from the volume of liquid are trapped in the plurality of micro-vortices.

2. The system according to claim 1, wherein the acoustic energy source comprises a piezoelectric transducer, wherein a voltage applied to the piezoelectric transducer is varied while the liquid flows through the first channel.

3. The system according to claim 1, further comprising a glass cover slip disposed between the device and the acoustic energy source.

4. The system according to claim 1, wherein the volume of liquid comprises a blood sample comprising red blood cells and plasma, and wherein the plurality of particles separated from the volume of liquid comprises the red blood cells.

5. The system according to claim 1, wherein the volume of liquid comprises a solution of nucleic acid, wherein nucleic acid in the solution of nucleic acid is fragmented by the plurality of micro-vortices.

6. The system according to claim 1, wherein the device further comprises:
an outlet for the first channel; and
a second inlet into the first channel and disposed between the first inlet and the outlet, wherein a second volume of gas is received via the second inlet and is inserted into the first channel.

7. The system according to claim 1, wherein the first channel is one channel of a plurality of channels, wherein sides of each channel of the plurality of channels are lined with a respective plurality of CATs, and wherein the plurality of channels and the pluralities of the CATs are integrated into one chip.

8. A system for manipulating particles in fluids, the system comprising:
an acoustic energy source configured to produce ultrasound;
a device disposed over the acoustic energy source and comprising:
a first channel;
a first inlet into the first channel, wherein a volume of liquid that is received via the first inlet flows in a direction through the first channel;
a first plurality of gas-liquid cavity acoustic transducers (CATs) lining a first side of the first channel, wherein each CAT of the first plurality of CATs is connected to the first channel at an angle so that a respective opening of each CAT of the first plurality of CATs faces toward the direction of flow of the volume of liquid through the first channel; and
a second plurality of CATs lining a second side of the first channel, wherein the second side is opposite the first side, wherein each CAT of the second plurality of CATs is connected to the first channel at an angle so that a respective opening of each CAT of the second plurality of CATs faces away from the direction of flow of the volume of liquid through the first channel;

wherein for each CAT of the first and second pluralities of CATs, a gas-liquid interface is created between the volume of liquid flowing through the first channel and a respective first volume of gas in the CAT, wherein the ultrasound produced from the acoustic energy source causes the gas-liquid interface to oscillate, thereby generating a plurality of micro-vortices in the first channel, wherein a plurality of particles in the volume of liquid are separated from the volume of liquid as the volume of liquid flows through the first channel, and wherein the plurality of particles separated from the volume of liquid are trapped in the plurality of micro-vortices.

9. The system according to claim 8, wherein the acoustic energy source comprises a piezoelectric transducer, wherein a voltage applied to the piezoelectric transducer is varied while the liquid flows through the first channel.

10. The system according to claim 8, further comprising a glass cover slip disposed between the device and the acoustic energy source.

11. The system according to claim 8, wherein the volume of liquid comprises a blood sample comprising red blood cells and plasma, and wherein the plurality of particles separated from the volume of liquid comprises the red blood cells.

12. The system according to claim 8, wherein the volume of liquid comprises a solution of nucleic acid, wherein nucleic acid in the solution of nucleic acid is fragmented by the plurality of micro-vortices.

13. The system according to claim 8, wherein the device further comprises:
an outlet for the first channel; and
a second inlet into the first channel and disposed between the first inlet and the outlet, wherein a second volume of gas is received via the second inlet and is inserted into the first channel.

* * * * *